(12) United States Patent
Ogura et al.

(10) Patent No.: US 8,149,987 B2
(45) Date of Patent: Apr. 3, 2012

(54) RADIATION IMAGING APPARATUS AND CONTROL METHOD FOR THE SAME

(75) Inventors: Takashi Ogura, Tokyo (JP); Osamu Tsujii, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 192 days.

(21) Appl. No.: 12/749,239

(22) Filed: Mar. 29, 2010

(65) Prior Publication Data

US 2010/0246759 A1    Sep. 30, 2010

(30) Foreign Application Priority Data

Mar. 31, 2009   (JP) ................................. 2009-087836

(51) Int. Cl.
    *A61B 6/04* (2006.01)
(52) U.S. Cl. .......................................... 378/37; 378/115
(58) Field of Classification Search .................. 378/145, 378/114–115, 124, 62, 122, 37
    See application file for complete search history.

(56) References Cited

U.S. PATENT DOCUMENTS

| | | | | |
|---|---|---|---|---|
| 6,333,968 B1 * | 12/2001 | Whitlock et al. | ............. | 378/136 |
| 2003/0035511 A1 | 2/2003 | Braess et al. | | |
| 2003/0194121 A1 | 10/2003 | Eberhard et al. | | |
| 2005/0078799 A1 | 4/2005 | Ancelin et al. | | |
| 2007/0189448 A1 | 8/2007 | Muller et al. | | |
| 2007/0237287 A1 | 10/2007 | Sukovic et al. | | |
| 2009/0316860 A1 | 12/2009 | Okunuki et al. | | |
| 2009/0323893 A1 * | 12/2009 | Hanke et al. | ..................... | 378/37 |
| 2010/0034450 A1 * | 2/2010 | Mertelmeier | ................. | 382/131 |
| 2010/0239064 A1 * | 9/2010 | Zhou et al. | ........................ | 378/9 |

FOREIGN PATENT DOCUMENTS

| | | |
|---|---|---|
| JP | 8-264139 A | 10/1996 |
| JP | 9-180894 A | 7/1997 |
| JP | 2004-329784 A | 11/2004 |
| JP | 2007-216022 A | 8/2007 |
| JP | 2007-265981 A | 10/2007 |
| WO | 2004/080309 A2 | 9/2004 |
| WO | 2009/012453 A1 | 1/2009 |

* cited by examiner

*Primary Examiner* — Hoon Song
(74) *Attorney, Agent, or Firm* — Canon U.S.A., Inc. IP Division (57) ABSTRACT

A radiation imaging apparatus that captures radiographic images includes a radioactive ray generating unit configured to irradiate a subject with a plurality of radioactive rays generated by a plurality of electron sources. A radioactive ray detection unit captures a plurality of first radiographic images based on detection of the plurality of radioactive rays that have passed through the subject at different irradiation angles. Area specification unit specifies an object area using the plurality of first radiographic images captured by the radioactive ray detection unit, and a determination unit determines an electron source to be driven from the plurality of electron sources based on the object area specified by the area specification unit, such that a second radiographic image is captured based on the radioactive rays generated by the electron source determined by the determination unit.

11 Claims, 10 Drawing Sheets

RADIATION IMAGING APPARATUS AND CONTROL METHOD FOR THE SAME

BACKGROUND OF THE INVENTION

1. Field of the Invention

The present invention relates to a radiation imaging apparatus and a control method for the same.

2. Description of the Related Art

A radioactive ray (for example X-ray) tube is configured to use a thermal electron source. An X-ray tube emits thermal electrons from a filament which is heated to high temperature and accelerates an electron beam to high energy via a Wehnet electrode, an extraction electrode, an acceleration electrode and a lens electrode. After forming the electron beam into a desired shape, X-rays are generated by irradiation of a metallic X-ray target with the beam.

In recent years, the thermo electron source has been replaced by the development of a cold-cathode electron source. Cold-cathode electron sources have been widely researched as application of flat panel displays (FPD). A representative example of a cold-cathode electron source is a Spindt-type electron source in which electrons are extracted by application of a high electrical field to a tip of a needle measuring tens of nanometer (nm). A surface conduction electron source is known. In a surface conduction electron source, an electron emitter formed from a carbon nanotube (CNT) or from a minute nm-order structure is formed on a surface of a glass substrate and electrons are emitted from the electron emitter.

As application of these electron sources, a technique has been discussed which generates X-rays by forming a single electron beam using a Spindt-type electron source or a CNT electron source as discussed in Japanese Patent Application Laid-Open No. 9-180894 and Japanese Patent Application Laid-Open No. 2004-329784. Further, Japanese Patent Application Laid-Open No. 8-264139 and J. Zhang "Stationary scanning X-ray source based on carbon nanotube field emitters" Applied Physics Letters 86, 184104 (2005), discuss a technique for generating X-rays by irradiation of an X-ray target using an electron beam from a multi electron source which uses a plurality of cold-cathode electron sources. Japanese Patent Application Laid-Open No. 2007-265981, which corresponds to patent application publication US 2009/0316860 and is assigned to the assignee of the present application, discusses a technique of using a multi X-ray source to generate a multi X-ray beam which has excellent properties and avoids mutual interference.

A radiation imaging apparatus has various applications. For example, one of those applications is a mammographic apparatus configured to execute mammography to acquire a radiographic image of a mammary gland, a tumor, or calcification. During mammography, a patient's breast is positioned in a special platform and compressed with a paddle made of clear plastic or the like. Breast compression is necessary, among other reasons, to even out the breast thickness so that all of the breast tissue can be evenly visualized, to spread the tissue so that small abnormalities are less likely to be obscured by tissue, to allow the use of lower X-ray dosage, to hold the breast still while imaging, to reduce X-ray scatter. Notwithstanding breast compression, since a mammographic apparatus provides a mammogram by projection, the mammary gland image sometimes may become blurred due to superimposition of the mammary gland with calcification or a tumor. Statistical data shows that approximately half of the cases in which mammogram re-scanning was required were caused by this type of superimposition with mammary gland tissue. In an attempt to address the superimposition problem, Japanese Patent Application Laid-Open No. 2007-216022 discusses a technique for generating a three-dimensional image in a suspect area of clinical concern by driving an X-ray source at a position along a direction of compression, acquiring a plurality of X-ray images from a group of exposures and using tomosynthesis to reconstruct the images.

Generally, a mammographic apparatus executes bidirectional imaging processing using a craniocaudal projection (CC projection) and a mediolateral oblique projection (MLO projection). With these techniques, images of the breast are captured from a direction along a compression direction. It is, however, sometimes desirable to vary the incident direction of X-ray radiation according to a calcification distribution profile or a tumor profile.

However, a suitable incident direction of X-ray cannot be known in advance. When executing radioscopic imaging other than mammography, a suitable imaging direction is determined and then high-resolution and high-dose still images are captured. When imaging breasts, since a mammographic X-ray source is conventionally positioned slightly higher than the head of a patient, a patient may experience discomfort during displacement of the X-ray source.

In addition, since the X-ray source executes imaging in a stationary state, when the X-ray source is displaced, the apparatus itself vibrates and residual vibration during imaging processing may adversely affect image definition. Moreover, time required for imaging will be increased is a waiting period is taken until such vibration dissipates. Further, a patient will experience considerable discomfort since the breast remains compressed during this time.

SUMMARY OF THE INVENTION

The present invention is directed to a radiation imaging apparatus and a control method for the same configured to acquire a radiographic image which prevents superimposition without requiring mechanical displacement of an electron source.

According to an aspect of the present invention, a radiation imaging apparatus configured to capture a radiographic image includes a radioactive ray generating unit having a plurality of electron sources configured to irradiate a subject with a plurality of radioactive rays generated at different radiation angles, a radioactive ray detection unit configured to capture a plurality of first radiographic images based on detection of the plurality of radioactive rays that have passed through the subject at the different irradiation angles, an area specification unit configured to specify an object area using the plurality of first radiographic images captured by the radioactive ray detection unit, and a determination unit configured to determine at least one electron source to be driven from the plurality of electron sources based on the object area specified by the area specification unit, wherein a second radiographic image is captured based on radioactive rays generated by the electron source determined by the determination unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

A radiation imaging apparatus and a control method for the same according to the present invention will be described in detail hereafter with reference to the attached drawings. In the exemplary embodiments below, the present specification describes X-rays as an example application of a radioactive ray. However, the radioactive ray is not limited to X-rays and may include electromagnetic waves, alpha rays, beta rays, gamma rays and the like. Similarly, in the embodiments described below, the description uses examples in which a radiation imaging apparatus according to the present invention is applied to a mammographic apparatus. It is to be understood that such a radiation imaging apparatus can be equally applied to other radiographic applications, such as imaging of other body parts of human or non-human patients.

Figure 1:
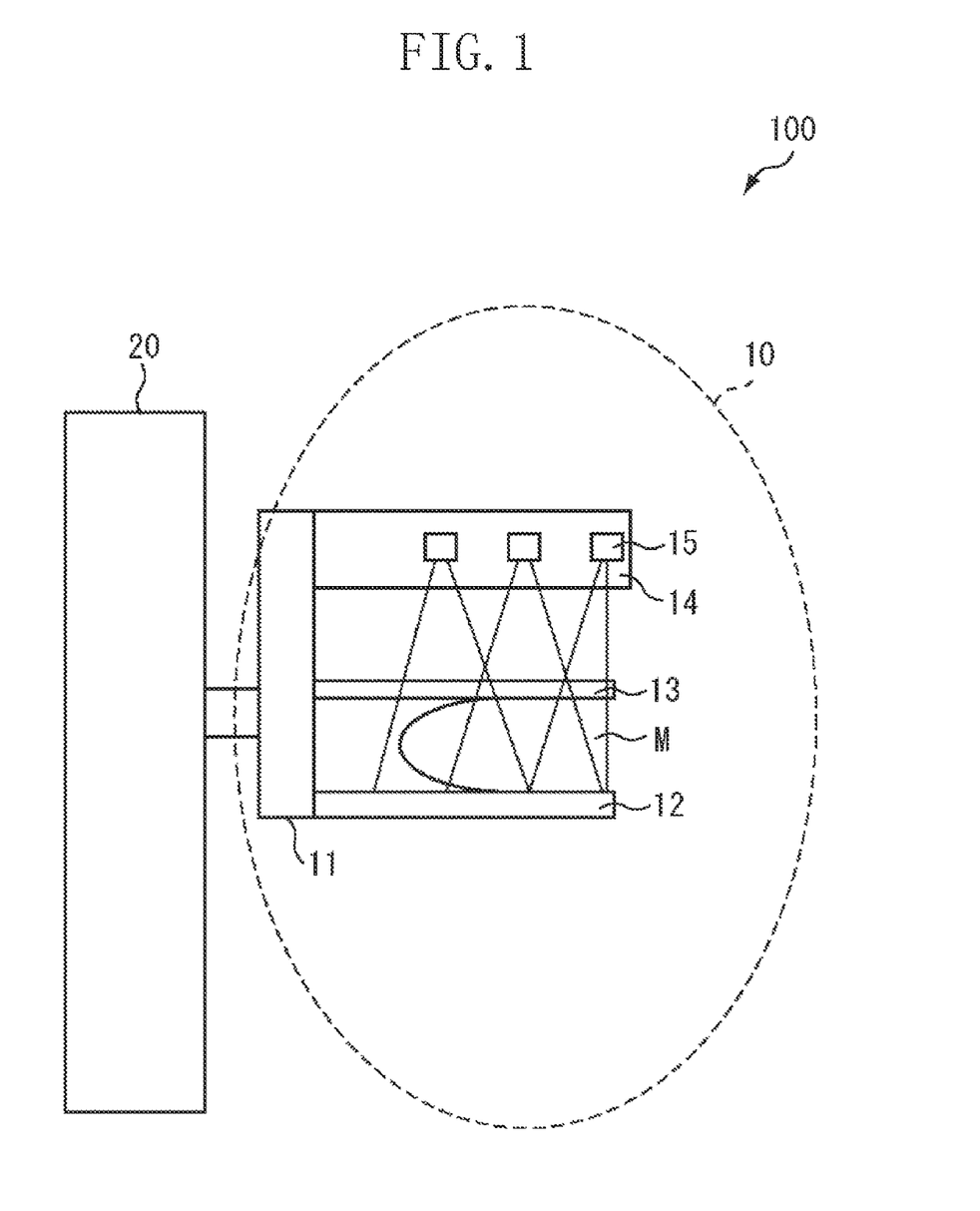
FIG. 1 illustrates an example of a configuration of a mammographic apparatus according to an exemplary embodiment of the present invention.

Initially, a first exemplary embodiment will be described with reference to the drawings of FIGS. 1 through 6. FIG. 1 illustrates an example of the configuration of a mammographic apparatus 100 according to the first exemplary embodiment of the present invention.

The mammographic apparatus 100 is provided with one or a plurality of computers. The computer includes a main control unit such as a central processing unit (CPU) and storage units such as a read only memory (ROM) and a random access memory (RAM). The computer may be provided with a communication unit such as a network card and an input/output unit such as a keyboard, mouse, display, or touch panel. These constitutive units are connected by a bus or the like and are controlled by the main control unit executing programs stored in the storage units.

The mammographic apparatus 100 is provided with an imaging apparatus 10 and a control apparatus 20. The imaging apparatus 10 is configured to capture X-ray images. The control apparatus 20 is configured to execute overall control of processing in the mammographic apparatus 100. A subject M is for example a breast of a patient (or other part of a human body).

The imaging apparatus 10 is provided with a C arm 11, a two-dimensional sensor 12, a compression plate 13 and a multi X-ray source generating unit 14.

The compression plate 13 compresses the breast to extend the breast thinly and is formed from a material which has sufficient strength and superior X-ray transmission properties. The C arm 11 is formed from an arm member in a shape of the letter "C". The multi X-ray source generating unit 14 and the two-dimensional sensor 12 are disposed in an opposed configuration on both ends of the C arm 11.

The multi X-ray source generating unit 14 functions as a radioactive ray generating unit configured to irradiate (expose) the subject (for example, a patient's body or a part thereof) with a plurality of radiation rays (X-rays). The multi X-ray source generating unit 14 may be implemented using a technique discussed for example in the above-referenced patent application publication US 2009/0316860, which is assigned to the assignee of the present application and is incorporated herein by reference.

Briefly described, in one embodiment, a plurality of electron emission elements 35 can be provided as electron sources (X-ray sources) in the multi X-ray source generating unit 14. An electron beam is emitted from each of the plurality of electron emission elements 35 to thereby irradiate a transmissive target 15 which consequently causes generation of X-rays to irradiate the subject.

Figure 2:
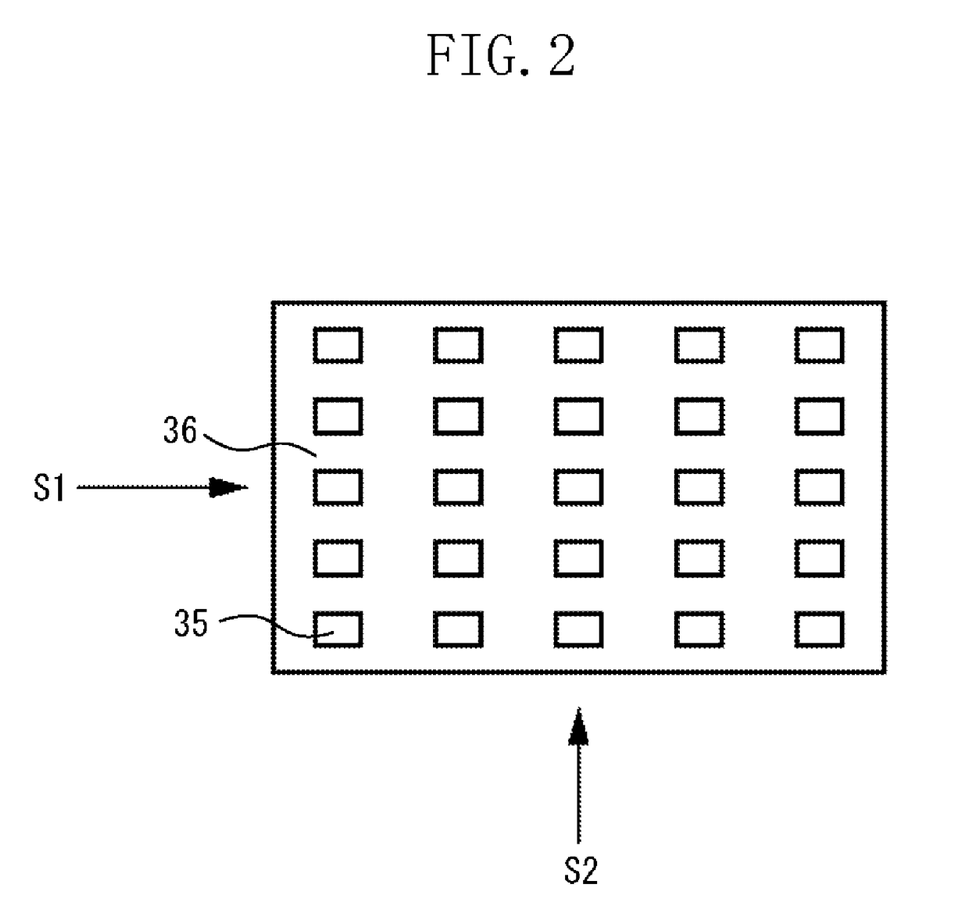
FIG. 2 illustrates an example of a configuration of a multi X-ray source generation unit illustrated in FIG. 1.

FIG. 2 illustrates an example of a configuration of a multi X-ray source generation unit 14. As illustrated in FIG. 2, the electron emission elements 35 are disposed in a two-dimensional N*M array on an element array 36. In other words, the emission elements 35 are disposed in a two-dimensional array on a plane which is orthogonal to the imaging direction of the X-ray image. The transmissive targets 15 (not labeled in FIG. 2) are disposed in a one to one correspondence with the electron emission elements 35 so that the X-rays from the whole or a part of the two-dimensional N*M points are irradiated towards the subject M (for example, the lower jaw of a patient) at different radiation angles. As illustrated in FIG. 2, the electron emission elements 35, which are positioned in correspondence with the transmissive targets 15, in the present exemplary embodiment are disposed in a two-dimensional array. However, in other embodiments, the emission elements 35 may be disposed in correspondence with the transmissive targets 15 in a one-dimensional array, a circular array, or in other arrangements.

A plurality of X-rays emitted from the transmissive targets 15 (X-ray focal points) of the multi X-ray source generating unit 14 passes via the compression plate 13 through the subject M and arrives at the two-dimensional sensor 12. In this manner, a plurality of X-ray images is captured using X-rays having a corresponding plurality of irradiation angles. An electron emission amount of each of the plurality of electron emission elements 35 is individually controlled by drive signals S1 and S2 from the control apparatus 20. In other words, a matrix signal formed by the drive signals S1 and S2 executes individual control of the electron emission amount from the element array 36, so that ON/OFF settings for a plurality of X-rays can be controlled.

The two-dimensional sensor 12 functions as a radioactive ray detection unit configured to detect X-rays that pass through the subject at different angles of irradiation. In this manner, the mammographic apparatus 100 captures X-ray images of the subject. The two-dimensional sensor 12 includes an amorphous selenium sensor or amorphous silicon. Overall external dimensions of the two-dimensional sensor 12 may be approximately 24 cm*30 cm.

Figure 3:
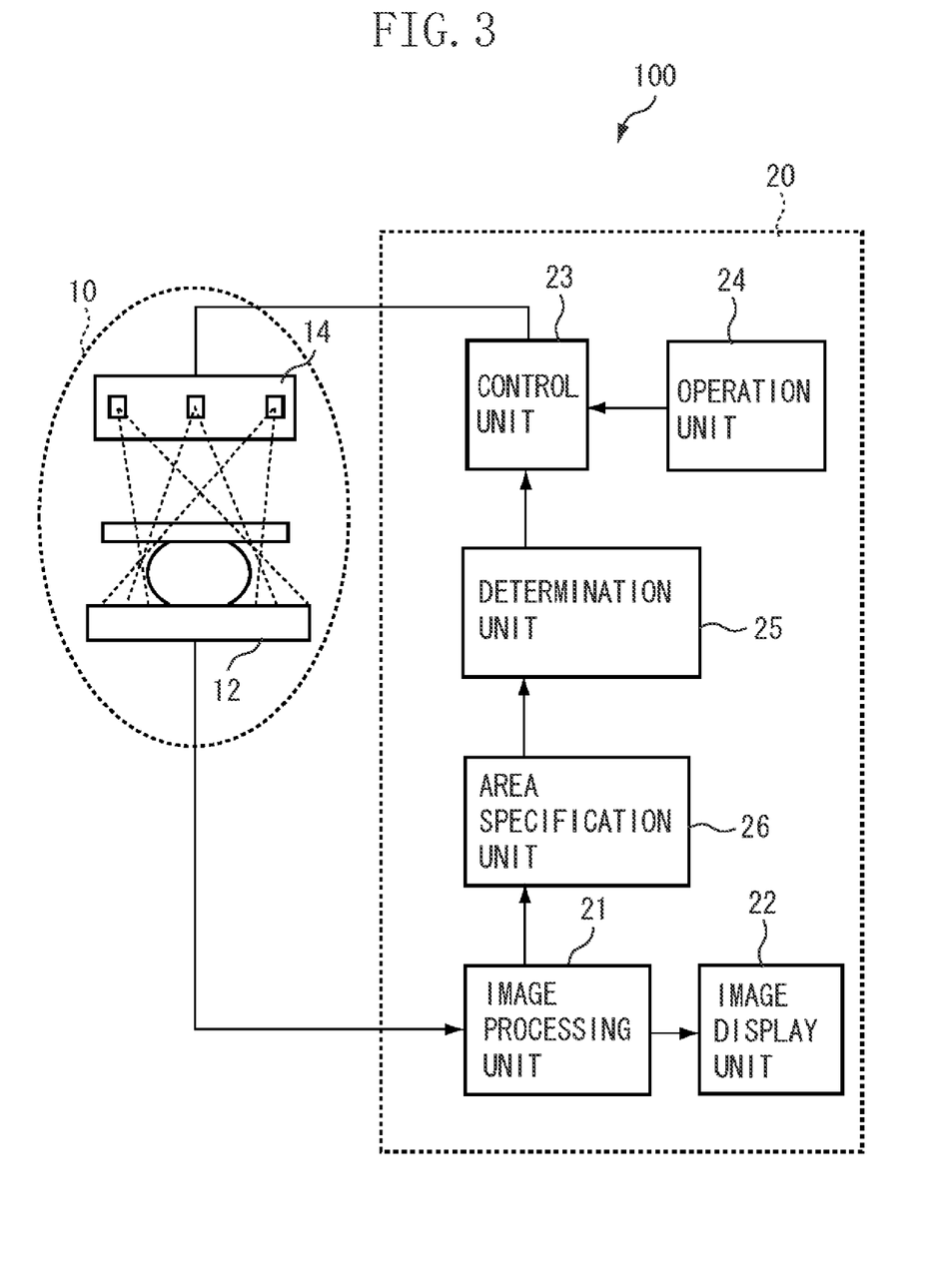
FIG. 3 illustrates an example of a functional configuration of a control unit illustrated in FIG. 1.

Next, an example of a functional configuration of the control apparatus 20 shown in FIG. 1 will be described by referring to the illustration of FIG. 3.

The functional configuration of the control apparatus 20 includes an image processing unit 21, an image display unit 22, a control unit 23, an operation unit 24, a determination unit 25 and an area specification unit 26.

The image processing unit 21 is configured to execute imaging processing of an X-ray image using an X-ray intensity distribution detected by the two-dimensional sensor 12. More specifically, reconstruction processing is applied to a plurality of X-ray images having different X-ray irradiation angles, so that a plurality of tomographic images is generated. The reconstruction processing may be executed, for example, using the filtered back-projection (FBP) technique. FBP calculation processing applies filter processing to a measured projection to thereby obtain a back projection image. The plurality of tomographic images produced by the reconstruction processing represents a parallel planar structure relative to the two-dimensional sensor 12. In other words, the plurality of tomographic images correlates to planes of different distance from the two-dimensional sensor 12.

The image display unit 22 is configured to display the X-ray images processed by the image processing unit 21. The image display unit 22 may be implemented, for example, by a liquid crystal display (LCD) panel or the like. The operation unit 24 is used to input instructions from a user to the apparatus (control apparatus 20). The operation unit 24 may be implemented, for example, by a mouse, a keyboard, a touch screen panel or the like. Moreover, the image display unit 22 and the operation unit 24 may be implemented as an integrated touch panel.

The area specification unit 26 specifies an object area in the plurality of X-ray images which have different X-ray irradiation angles. More specifically, the area specification unit 26 specifies an object area in the plurality of tomographic images generated by the image processing unit 21. The object area indicates an area including a lesion area such as a mammary gland distribution, a tumor profile, and a calcification distribution profile indicating a clustered, linear or segmental distribution indicative of malignancy. A lesion area shadow often has a characteristic density distribution. Consequently, the area specification unit 26 uses these density characteristics to specify an area estimated of the lesion area as an object area.

Methods for implementing an algorithm for specifying an object area of an image are known and therefore detailed description thereof will be omitted. Briefly, however, an algorithm for specifying a tumor may employ an Iris filter (for example, see Japanese Patent Application Laid-Open No. 8-263641). Alternatively, or in addition thereto, an algorithm for specifying calcification may employ a morphological filter (for example, see Japanese Patent Application Laid-Open No. 8-272961).

The determination unit 25 determines one or more of the X-ray sources to be driven from a plurality of X-ray sources. In one embodiment, the determination unit 25 may determine one or more of the electron emission elements 35 provided in the two-dimensional N*M array of FIG. 2. The determination of the X-ray source to be driven firstly uses the object area specified by the area specification unit 26 to calculate an irradiation surface area for the object area corresponding to each irradiation direction and then derives an irradiation direction to minimize or maximize the irradiation surface area from calculated results. An X-ray source enabling irradiation from the derived irradiation direction is then selected from among the plurality of X-ray sources. Accordingly, the X-ray source to be driven can be selectively determined based on the object area specified by the area specification unit.

Figure 4:
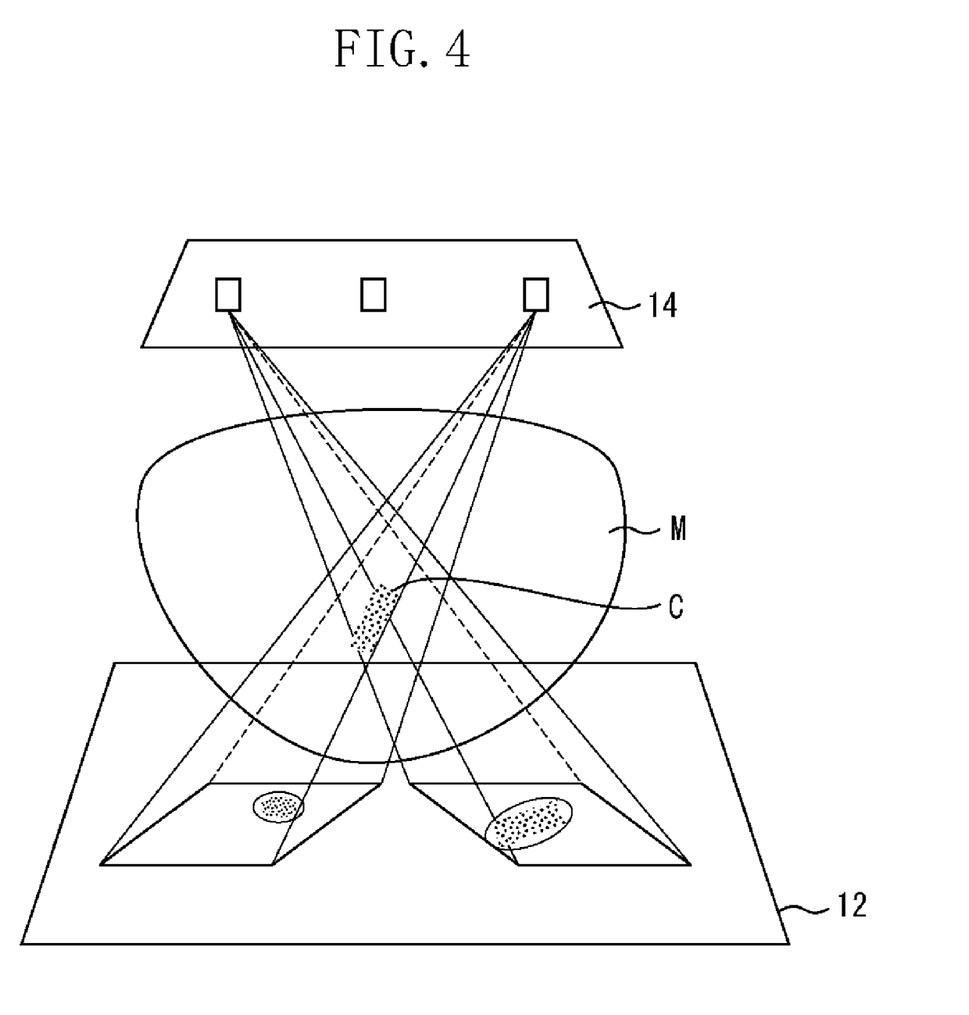
FIG. 4 is a first diagram illustrating a general process executed by a determination unit illustrated in FIG. 3.

Next, a first general process executed by a determination unit 25 is described in accordance with the illustration of FIG. 4. When a tumor is present in the object area, for example, the calculation of the irradiation surface area is determined based on a surface area of the tumor. When a plurality of portions of calcification is present in the object area, the area encompassing the plurality of portions of calcification is approximated to a sphere and a surface area of that sphere is calculated. The calculated value is used as the irradiation surface area. As illustrated in FIG. 4, the irradiation surface area of the object area varies according to the irradiation direction. Although FIG. 4 illustrates X-ray irradiation within a limited range for the purpose of facilitating description, the irradiation area is not limited thereby and, for example, the entire breast may be used or, for example, irradiation may be executed across a broad range.

Figure 5:
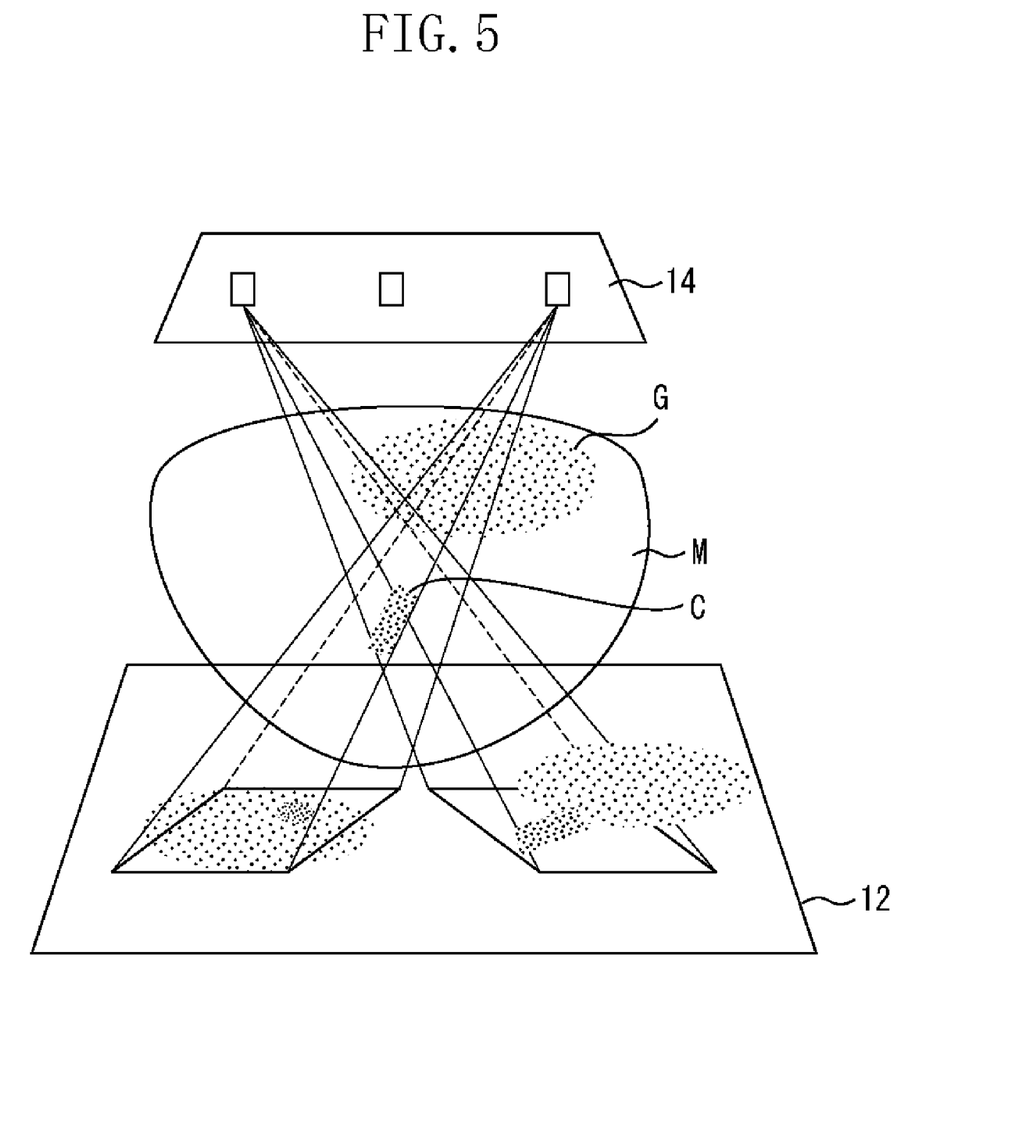
FIG. 5 is a second diagram illustrating a general process executed by the determination unit illustrated in FIG. 3.

Indeed, FIG. 5 illustrates a second general process executed by a determination unit 25 where a broad range irradiation area is processed. However, as illustrated in FIG. 5, an irradiation direction may result in superimposition of a mammary gland G with a lesion area C such as calcification, a tumor, an implant or the like. A superimposition of this sort may have an adverse affect on visual definition of the lesion areas. In this case, the determination unit 25 determines an irradiation direction from which an appropriate X-ray image can be captured, and selects the X-ray source corresponding to the determined irradiation radiation. The thus captured X-ray image facilitates discrimination of the mammary gland G from the lesion area C.

When the mammary gland G is superimposed with the lesion area C, a contrast between the lesion area and its peripheral sections (within a predetermined range from the lesion area) is reduced. Therefore, the X-ray source may be selected using this reduction of contrast. In other words, the difference in an average pixel number between the lesion area (namely, the object area) is compared with peripheral sections thereto and a direction in which the difference in the average pixel value is maximized is determined. Consequently, an X-ray source is selected which can emit X-ray from that direction.

The control unit 23 is configured to execute overall control of each constitutive unit of the control apparatus 20. For example, the control unit 23 uses the determination result from the determination unit 25 to control X-ray irradiation using the X-ray source. Although not illustrated in FIG. 3, the control unit 23 is operatively connected with each constitutive unit of the control apparatus 20.

The above description of the processes illustrated in FIGS. 4 ad 5 is used an example of a configuration of the mammographic apparatus 100. It will be evident to a person of ordinary skill in the art that the configuration of the apparatus 100 need not always be executed in accordance with the configuration illustrated in the drawings. For example, each of the functional configurations above may be disposed respectively in a plurality of apparatuses and implemented as a system.

Next, an example of a flow of imaging processing in the mammographic apparatus 100 illustrated in FIG. 1 will be described in reference to FIG. 6. The description will use an example of processing when a lesion area is present.

When processing is commenced, in step S101, the mammographic apparatus 100 captures a first radiographic image. More specifically, a plurality of X-rays is irradiated toward the subject (for example, a human body or a part thereof) and a plurality of X-ray images having different X-ray irradiation angles is captured.

When the image capturing is completed, in step S102, the image processing unit 21 of the mammographic apparatus 100 executes reconstruction processing on the plurality of X-ray images having different X-ray irradiation angles to generate a plurality of tomographic images.

In step S103, the area specification unit 26 of the mammographic apparatus 100 uses the plurality of tomographic images generated by the image processing unit 21 to specify an object area. As described above, the object area indicates an area in which a mammary gland or a lesion area such as a tumor or calcification is imaged.

In step S104, the determination unit 25 of the mammographic apparatus 100 determines an X-ray source to be driven from the plurality of X-ray sources. As described above, the determination of the X-ray source is executed by firstly using the object area specified by the area specification unit 26 to calculate an irradiation surface area of the object area corresponding to each irradiation direction and then determining the irradiation direction which maximizes or minimizes the irradiation surface area. Then an X-ray source is selected from the plurality of X-ray sources to enable irradiation from the determined direction. In this manner the X-ray source to be driven is determined.

When the X-ray source to be driven is determined, the mammographic apparatus 100 executes imaging of a second radiographic image. The second radiographic image is used in diagnosis and is captured with a higher resolution and a higher X-ray dosage amount than the first radiographic image. In step S105, the mammographic apparatus 100 captures an X-ray image by irradiating X-rays from the X-ray source determined in step S104.

The second radiographic image is captured by irradiating X-rays using a larger tube current or longer irradiation time (exposure time) than the imaging processing in step S101. The tube current or length of irradiation time may be determined (automatically or by user analysis), for example, by using a signal/noise ratio (S/N ratio) of the first radiographic image. When considering a S/N ratio, an evaluation of the relationship of S/N ratio and image quality of the first image may be necessary. Accordingly, for example, the lower the S/N ratio of the first image, the larger the tube current or the longer the irradiation time for imaging processes of the second image would be required.

In the imaging processing in step S101, it is not necessary to irradiate X-rays using all X-ray sources. For example, after specifying a lesion area based on the X-ray image captured using part of the plurality of the X-ray sources, a point corresponding to the lesion area among the plurality of X-ray images (tomographic images) is determined and the corresponding point is used to predict the irradiation direction which minimizes or maximizes the irradiation surface area. That prediction result may be used to determine the X-ray source to be driven.

Figure 6:
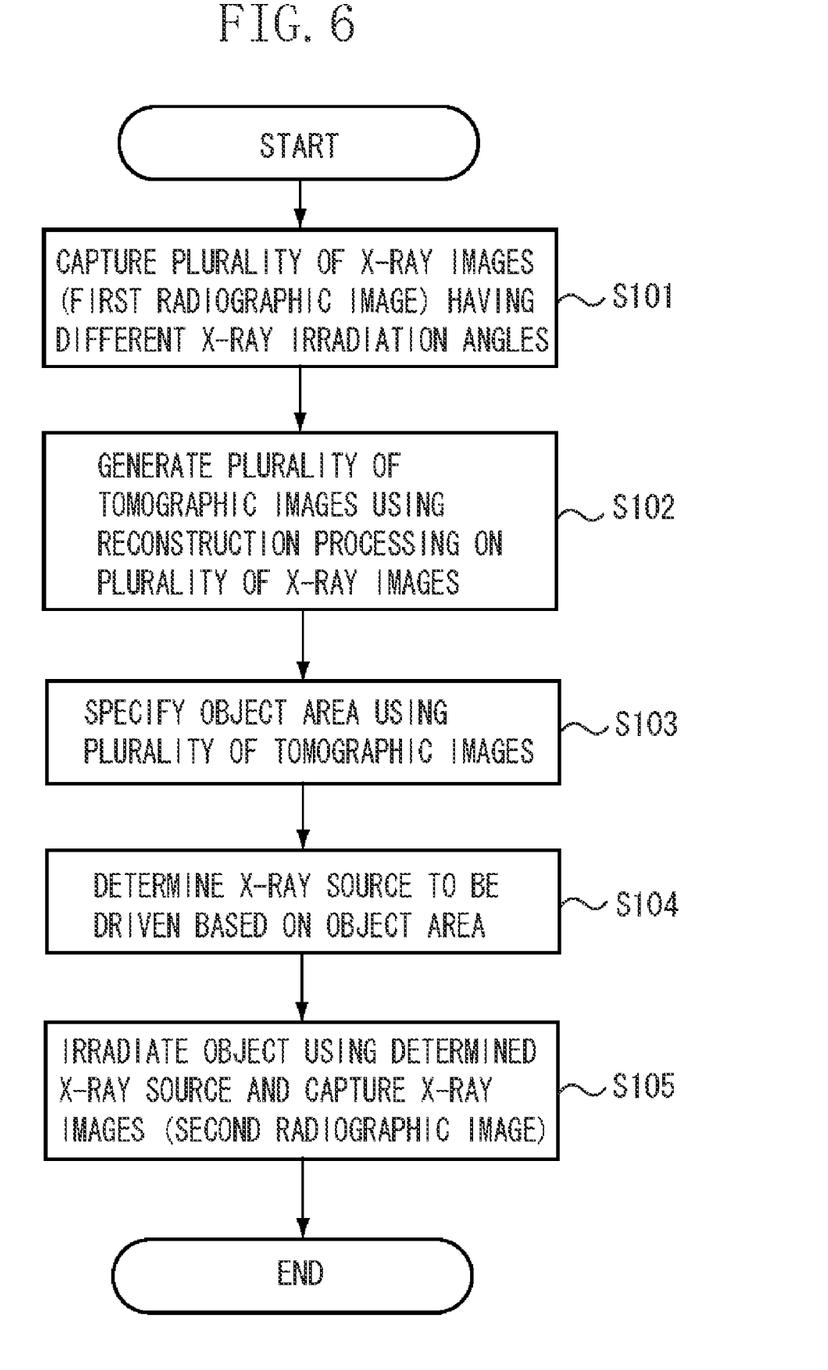
FIG. 6 is a flowchart illustrating an example of the flow of imaging processing in the mammographic apparatus illustrated in FIG. 1.

In FIG. 6, although the processing when a lesion area is present is described in the processing in step S103, an X-ray image may be captured by irradiating X-rays using an X-ray source in a predetermined position when a lesion area is not specified. More specifically, in step S104, the X-ray source in the predetermined position is selected and the X-ray image is captured in step S105. The X-ray source in the predetermined positioned may, for example, be an X-ray source in a standard position such as a central position.

According to the above described first exemplary embodiment, a plurality of X-ray images (first radiographic images) with different X-ray irradiation angles is captured. An X-ray source to be driven is determined based on the plurality of X-ray images and X-rays are irradiated using the determined X-ray source to capture an X-ray image (second radiographic image).

Accordingly, X-ray images which avoid or minimize adverse effects resulting from distribution of mammary glands or superimposition thereof, and facilitate lesion area diagnosis can be efficiently acquired. For example, since the X-ray source is only switched electrically and is not mechanically displaced, the imaging time can be reduced. In addition, a patient comfort improved because there is no mechanical displacement of the X-ray source.

Next a second exemplary embodiment of the present invention will be described with reference to FIGS. 7, 8A and 8B. The second exemplary embodiment describes disposition relationship of a grid 81 and the X-ray source of the mammographic apparatus 100. The structural configuration and processing of the mammographic apparatus 100 according to the second exemplary embodiment is similar to that described in reference to the first exemplary embodiment and description thereof will be omitted.

Figure 7:
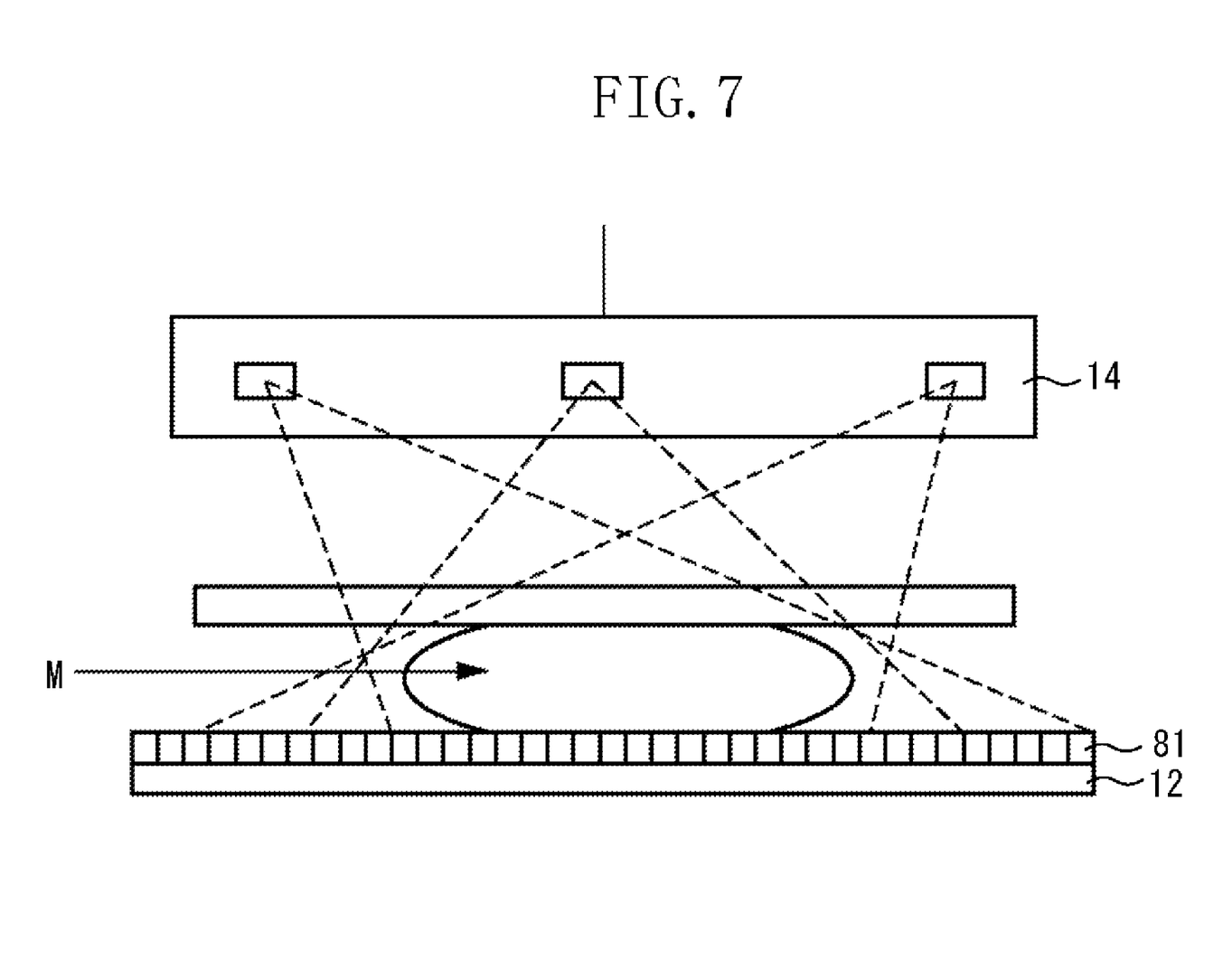
FIG. 7 illustrates an example of a grid disposed between a subject and a detection unit.

In the second embodiment, as illustrated in FIG. 7, a collimator or grid 81 is disposed between the subject M and the two-dimensional sensor 12 and is configured to use striped lead foil to absorb scatter radiation scattered by the subject M. In this manner, only X-rays passing linearly from the X-ray source through the subject M are selectively incident upon the two-dimensional sensor 12.

The lead foil of the grid 81 has a configuration to converge toward a point light source, so that if a position of an X-ray deviates, the X-ray will not pass through the grid even if it is linear. (See for example, Japanese Patent Application Laid-Open No. 09-066054).

Figures 8A, 8B:
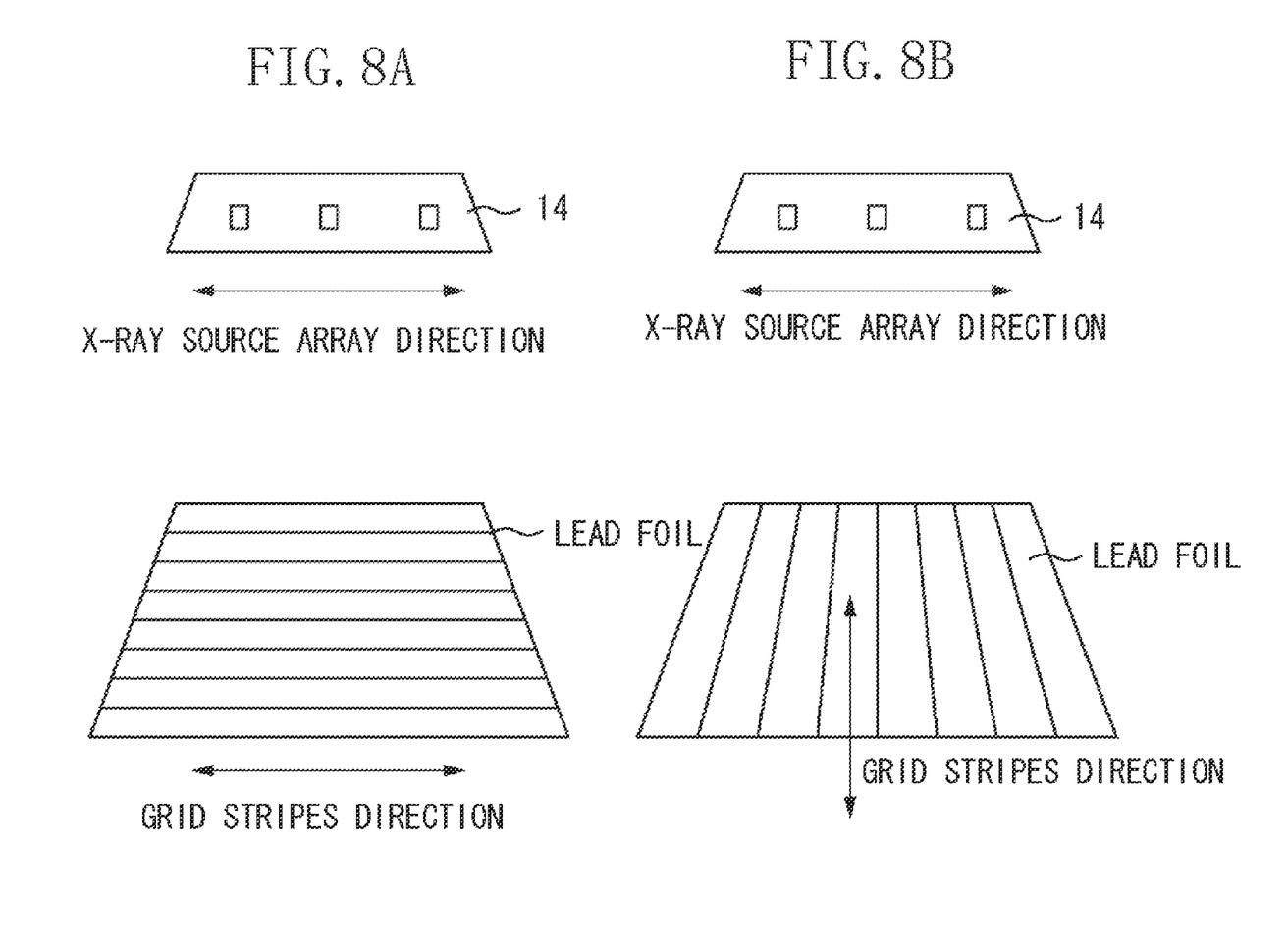
FIGS. 8A and 8B illustrate exemplary directions of grid stripes.

As illustrated in FIG. 8B, when the X-ray source generating unit 14, or more specifically, the transmissive target 15 (not labeled), is arrayed in one dimension in a direction which is perpendicular to grid stripes, even linear X-rays from the X-ray source are not transmitted through the grid. Consequently, the mammographic apparatus 100 according to the second exemplary embodiment is preferably configured so that the array direction of the plurality of X-ray sources is parallel to the stripe direction of the grid 81, as illustrated in FIG. 8A.

The second exemplary embodiment above can obtain a similar effect to the first exemplary embodiment and acquire an X-ray image which avoids cut-off resulting from the grid.

Figure 9:
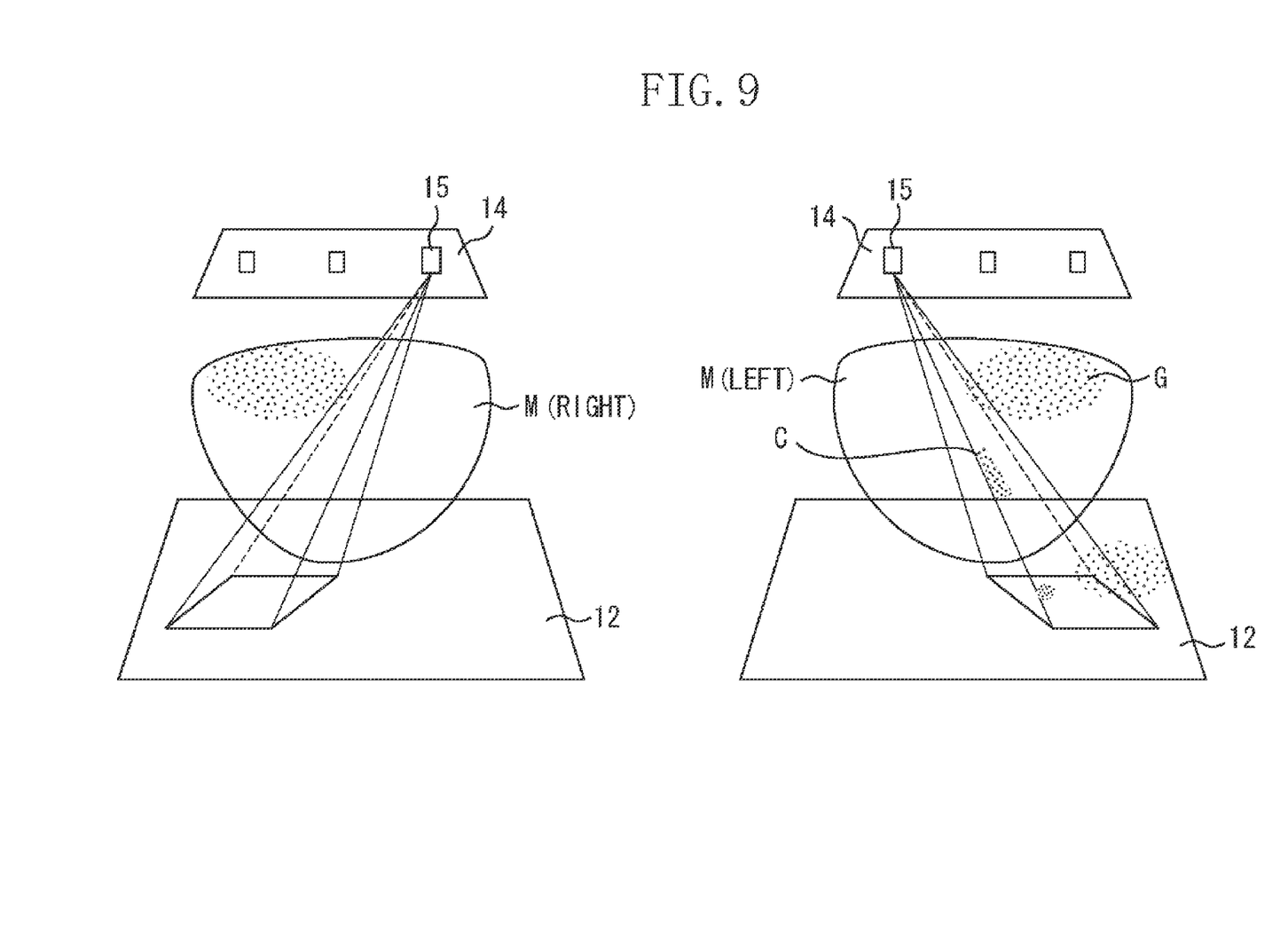
FIG. 9 illustrates an example of a processing flow for imaging right and left breasts.

Next, a third exemplary embodiment will be described with reference to FIG. 9. In the third exemplary embodiment, processing flow for imaging the right and left breasts is described. The configuration or processing of the mammographic apparatus 100 according to the third exemplary embodiment is similar to that described in reference to the first exemplary embodiment and therefore description thereof will be omitted.

The processing flow for imaging the right and left breasts will be described according to FIG. 9. The flow of imaging processing is basically similar to the flow described in FIG. 6 according to the first exemplary embodiment.

In the third embodiment, the mammographic apparatus 100 firstly captures a plurality of X-ray images (first radiographic image) with different X-ray irradiation angles. As illustrated in FIG. 9, it is assumed for example that the presence of a lesion area C such as a calcification or tumor has been confirmed in the left breast. In this case, the mammographic apparatus 100 irradiates X-rays from a direction which will not be adversely affected by the mammary gland distribution as described in the first exemplary embodiment. After irradiation, an X-ray image of the left breast (second radiographic image) is captured. As described above in reference to the first embodiment, the second radiographic image is used in diagnosis and is captured with a higher resolution and a higher X-ray dosage amount than the first radiographic image.

The imaging of the other breast (right breast) is executed by irradiating X-rays using the X-ray source used in imaging of the left breast and an X-ray source provided at a symmetrical position on a plane on which the X-ray source is disposed in two-dimensions (or one-dimension). Since the irradiation direction of the X-rays is symmetrical, the right and left breast images are also symmetrical which thereby facilitates diagnosis comparison of the right and left breast.

When the lesion area C is not present (right breast illustrated in FIG. 9), imaging is executed by irradiating X-rays using an X-ray source in the standard position, for example, in the central position. When a lesion area is not present in the other breast, imaging is also executed by irradiating the other breast with X-rays from the central X-ray source.

However, when the left breast with the lesion area C is imaged after imaging of the right breast, the X-ray imaging processing is executed by irradiating X-rays from the direction which is not adversely affected by the distribution of the mammary glands in accordance with the procedure described in the first exemplary embodiment. If considerable differences in symmetric properties become apparent when the X-ray image of the previously-captured right breast without a lesion area is compared with the X-ray image of the subsequently-captured left breast with the lesion area, imaging of the previously-captured right breast is executed again. For example, when the surface area of the breast section in the right and left images are compared and a difference is greater than or equal to a fixed value, imaging may be re-executed.

The third exemplary embodiment above can obtain a similar effect to the first exemplary embodiment and acquire an X-ray image configured to facilitate comparative interpretation of conditions in the right and left breasts.

Next, a fourth exemplary embodiment will be described with reference to FIG. 10. The fourth exemplary embodiment describes a mammographic apparatus 100 which is provided with a fine needle aspiration biopsy function. More specifically, when a calcification or the like is discovered which has a clustered, linear or segmented distribution presenting indications of malignancy, qualitative determination of malignancy or benignancy is required. In this case, a fine needle aspiration biopsy is performed. In a fine needle aspiration biopsy, an aspiration needle (biopsy needle) is inserted into the breast to cytologically sample tissue suspected of malignancy including calcification or the like. The configuration or processing of the mammographic apparatus 100 according to the fourth exemplary embodiment is basically similar to the first exemplary embodiment and therefore only important points of difference will be described.

Figure 10:
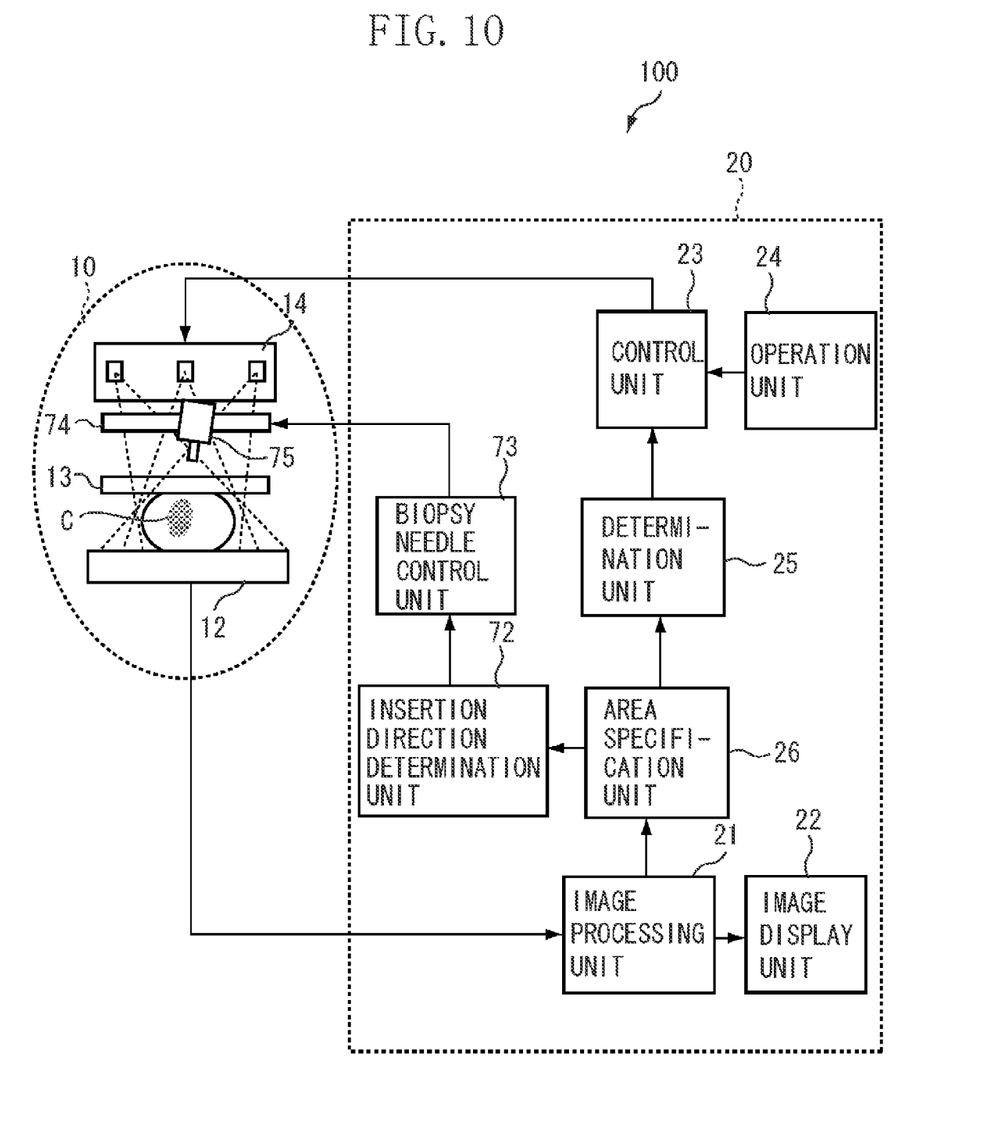
FIG. 10 illustrates a configuration of a control unit according to another exemplary embodiment.

FIG. 10 illustrates the functional configuration of a control apparatus 20 according to the fourth exemplary embodiment of the present invention.

The functional configuration of the control apparatus 20 includes an image processing unit 21, an image display unit 22, a control unit 23, an operation unit 24, a determination unit 25, an area specification unit 26, an insertion direction determination unit 72 and a biopsy needle control unit 73. A biopsy needle displacement unit 74 and a biopsy needle 75 are added to the imaging apparatus 10.

The operation unit 24 serves as an area designation unit used by an operator to designate an area for sampling of the lesion area from the breast. The operation unit 24 for example may be implemented by a mouse, keyboard or the like. The image display unit 22 and the operation unit 24 may be implemented as an integrated touch panel.

The insertion direction determination unit 72 determines an insertion direction (insertion angle) of the biopsy needle 75 to the lesion area designated by the operation unit 24. The insertion direction is determined as a direction from which more effective sampling of the lesion area can be acquired. The determination of the direction is executed based on density characteristics of the plurality of tomographic images generated by the image processing unit 21.

For example, when a plurality of portions of calcification is present, the plurality of tomographic images is used to determine an insertion direction as a direction which can pass through a center of gravity of each of the plurality of portions of calcification. In addition, the insertion direction of the biopsy needle 75 may be a direction having an entry path of the biopsy needle 75 which does not include a large blood vessel.

The biopsy needle displacement unit 74 moves the biopsy needle 75. The biopsy needle control unit 73 controls the biopsy needle 75. More specifically, the biopsy needle displacement unit 74 is controlled cased on the insertion direction determined by the insertion direction determination unit 72. In this manner, the position and insertion angle of the biopsy needle 75 can be controlled and inserted into the lesion area.

A processing flow of fine needle aspiration biopsy cytology will be briefly described below.

Cytology refers to a branch of pathology, the medical specialty that deals with making diagnoses of diseases and conditions through the examination of tissue samples from a patient's body. Accordingly, when a lesion area C is detected, an operator refers to a previously captured mammogram and fixes a breast of a patient to the compression plate 13 so that the lesion area C is in the center of the two-dimensional sensor 12. After fixing the breast, the mammographic apparatus 100 executes imaging by irradiating X-rays from various angles. The mammographic apparatus 100 displays the captured images on the image display unit 22. The displayed images may be one-dimensional images or tomographic images.

The operator refers to the plurality of displayed images and operates the operation unit 24 to specify an area of the lesion area C. According to the specification made by the operator, the insertion direction determination unit 72 of the mammographic apparatus 100 determines an insertion direction (insertion angle) of the biopsy needle 75. The insertion direction is determined, for example, based on the density characteristics of the plurality of tomographic images generated by the image processing unit 21. Thereafter, the biopsy needle control unit 73 of the mammographic apparatus 100 uses the determined insertion direction to control the position and insertion angle of the biopsy needle 75. In this manner, the biopsy needle 75 is inserted into the lesion area C to cytologically perform a minimally invasive evaluation of the lesion area.

Although the above description used an example of an operator using the operation unit 24 to specify an area for sampling of the lesion area from the breast, the present invention is not limited in this regard. For example, a three-dimensional position measurement unit may be configured to automatically calculate a three-dimensional position according to an X axis, Y axis and Z axis of a lesion area based on the object area specified by the area specification unit 26 and automatically sample the lesion area using the calculation result.

The fourth exemplary embodiment as described above can provide advantages similar to realized by the first exemplary embodiment. In addition, the fourth embodiment uses a plurality of tomographic images or the like to determine an insertion direction and position for the biopsy needle 75, so that an operator may safely insert the biopsy needle 75. In this manner, a fine needle aspiration biopsy can be executed using a single examination apparatus in a time efficient manner and without placing a large burden on a patient. For example, a radiographic image can be obtained without adverse effects resulting from superimposition or the distribution of mammary glands and without mechanically displacing the electron source. Furthermore, since the electron source is only switched electrically and is not mechanically displaced, the imaging time can be reduced.

Examples of representative exemplary embodiments of the present invention have been described above. However the invention is not limited to the exemplary embodiments as described above or in the attached drawings and may be suitably modified without departing from the spirit of the invention.

The present invention may be embodied as a system, apparatus, method, program or recording medium. More specifically, the present invention may be applied to a system formed from a plurality of devices or to an apparatus formed from a single device.

Furthermore, the processing as described above may be configured by a program installed on a computer. The program of course may be provided by a communication structure such as a network, but is may also be provided by storing on a recording medium such as a compact disc read only memory (CD-ROM), the like.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-087836 filed Mar. 31, 2009, which is hereby incorporated by reference herein in its entirety.

What is claimed is:

1. A radiation imaging apparatus configured to capture radiographic images, the radiation imaging apparatus comprising:
   a radioactive ray generating unit having a plurality of electron sources configured to irradiate a subject with a plurality of radioactive rays generated at different radiation angles;
   a radioactive ray detection unit configured to capture a plurality of first radiographic images based on detection of the plurality of radioactive rays that have passed through the subject at the different irradiation angles;
   an area specification unit configured to specify an object area using the plurality of first radiographic images captured by the radioactive ray detection unit; and
   a determination unit configured to determine at least one electron source to be driven from the plurality of electron sources based on the object area specified by the area specification unit,
   wherein a second radiographic image is captured based on radioactive rays generated by the electron source determined by the determination unit.

2. The radiation imaging apparatus according to claim 1, further comprising,
   an image processing unit configured to execute reconstruction processing on the plurality of first radiological images to generate a plurality of tomographic images, and
   wherein the area specification unit specifies the object area based on the plurality of tomographic images generated by the image processing unit.

3. The radiation imaging apparatus according to claim 1, wherein the determination unit calculates an irradiation surface area of the object area corresponding to a plurality of irradiation directions based on the object area specified by the area specification unit and determines an electron source to be driven based on the irradiation surface area.

4. The radiation imaging apparatus according to claim 3, wherein the electron source to be driven determined by the determination unit is capable of irradiating the subject with radioactive rays from an irradiation direction in which the irradiation surface area is maximized or minimized.

5. The radiation imaging apparatus according to claim 1, wherein the determination unit compares a difference of average pixel values between the object area specified by the area specification unit and an area within a predetermined range from the object area, and determines the electron source to be driven as one of the plurality of electron sources capable of irradiating the subject with radioactive rays from a direction in which the difference in the average pixel values is maximized.

6. The radiation imaging apparatus according to claim 1, further comprising:
   a grid which is disposed between the subject and the radioactive ray detection unit,
   wherein the grid includes striped lead foil and is configured to absorb scatter radioactive rays scattered by the subject, and
   wherein an array direction of the plurality of electron sources which are arrayed in one dimensional array and a stripe direction of the grid are parallel.

7. The radiation imaging apparatus according to claim 1, wherein the subject is a human breast, and
   wherein, when the second radiographic image of a left breast is captured, the determination unit determines the electron source to be driven as one of the plurality electron sources disposed in a position symmetrical to the electron source which is driven during imaging of a right breast.

8. The radiation imaging apparatus according to claim 1, wherein the subject is a human breast, and
   the radiation imaging apparatus further comprises:
   an insertion direction determination unit configured to determine a direction for insertion of a biopsy needle based on the plurality of first radiographic images captured by the radioactive ray detection unit; and
   a biopsy needle control unit configured to control insertion of the biopsy needle into the breast in the direction determined by the insertion direction determination unit.

9. The radiation imaging apparatus according to claim 1, wherein the second radiographic image is captured using a larger tube current or longer irradiation time than when the first radiographic image is captured.

10. The radiation imaging apparatus according to claim 1, wherein the subject is a human breast, and
    the object area includes any one of mammary gland distribution, a tumor profile or calcification distribution.

11. A method for capturing radiographic images with a radiation imaging apparatus, the method comprising:

irradiating a subject with a plurality of radioactive rays generated by using a plurality of electron sources disposed in a one-dimensional or two-dimensional array;

capturing a plurality of first radiographic images based on detection of a plurality of radioactive rays that have passed through the subject at different irradiation angles;

specifying an object area based on the captured plurality of first radiographic images;

determining an electron source to be driven from the plurality of electron sources based on the specified object area; and capturing a second radiographic image based on radioactive rays generated by the electron source determined at the determining step.

* * * * *